United States Patent [19]

Ludmerer

[11] Patent Number: 5,922,588

[45] Date of Patent: Jul. 13, 1999

[54] SYNTHETIC HPV16 VIRUS-LIKE PARTICLES

[75] Inventor: Steven Ludmerer, Piscataway, N.J.

[73] Assignee: Merck & Co., Inc., Rahway, N.J.

[21] Appl. No.: 08/943,583

[22] Filed: Oct. 3, 1997

Related U.S. Application Data

[XX .
[60] Provisional application No. 60/026,763, Oct. 4, 1996.
[51] Int. Cl.$^6$ .............................. C12N 7/00; C12N 7/01; A61K 39/12; C07K 14/025
[52] U.S. Cl. .................................. 435/235.1; 424/204.1; 530/350
[58] Field of Search ...................... 435/235.1; 424/204.1; 530/350

[56] References Cited

PUBLICATIONS

Christensen et al, 1994, Virology, vol. 205, pp. 329–335.
Heino et al, 1995, Journal of General Virology, vol. 76, pp. 1141–1153.

Kirnbauer et al, 1993, Journal of Virology, vol. 67, pp. 6929–6936.

Kirnbauer et al., 1994, Journal of the National Cancer Institute, vol. 86, No. 7, pp. 494–499.

Christensen, N. D. et al. Surface Conformational and Linear Epitopes on HPV–16 and HPV–18 L1 Virus–like Particles as Defined by Monoclonal Antibodies Virology 223, (1996) pp. 174–184.

*Primary Examiner*—Mary E. Mosher
*Assistant Examiner*—Ali R. Salimi
*Attorney, Agent, or Firm*—Joanne M. Giesser; Jack L. Tribble

[57] ABSTRACT

The invention is a series of synthetic virus-like particles useful in the characterization of human papillomavirus infection and assays employing the synthetic virus-like particles.

1 Claim, 3 Drawing Sheets

```
HPV11   N K Y D D V E N S G G Y G G N P G Q D N R V N V G M D   147
HPV16           L         T   A S   A Y A A   A         V   E C I S   150
```

FIG.1

```
                                                                ..148
HPV16     L N K L D D T E N A S A Y A A N A G V D N R E C I S
HPV16:5   L N K Y D D T E N A G G Y A A N A G Q D N R V C I S
HPV16:8   L N K Y D D T E N A G G Y G G N P G Q D N R V C I S
HPV16:10  L N K Y D D V E N S G G Y G G N P G Q D N R V C I S
```

SYNTHETIC HPV16 VIRUS-LIKE PARTICLES

CROSS-REFERENCE TO RELATED APPLICATIONS

This application claims the benefit of the provisional U.S. application Ser. No. 06/026,763 filed Oct. 4, 1996.

STATEMENT REGARDING FEDERALLY-SPONSORED R&D

Not applicable

REFERENCE TO MICROFICHE APPENDIX

Not applicable

FIELD OF THE INVENTION

The present invention is a series of synthetic virus-like particles (VLP) useful in the characterization of human papillomavirus infection and assays employing the synthetic virus-like particles.

BACKGROUND OF THE INVENTION

Papillomavirus infections occur in a variety of animals, including humans, sheep, dogs, cats, rabbits, monkeys, snakes and cows. Papillomaviruses infect epithelial cells, generally inducing benign epithelial or fibroepithelial tumors at the site of infection. Papillomaviruses are species specific infective agents; a human papillomavirus cannot infect a nonhuman animal.

Papiromaviruses may be classified into distinct groups based on the host that they infect. Human papillomaviruses (HPV) are further classified into more than 60 types based on DNA sequence homology (for a review, see Papillomaviruses and Human Cancer, H. Pfister (ed.), CRC Press, Inc., 1990). Papillomavirus types appear to be type-specific immunogens in that a neutralizing immunity to infection to one type of papillomavirus does not confer immunity against another type of papillomavirus.

In humans, different HPV types cause distinct diseases. HPV types 1, 2, 3, 4, 7, 10 and 26–29 cause benign warts in both normal and immunocompromised individuals. HPV types 5, 8, 9, 12, 14, 15, 17, 19–25, 36 and 46–50 cause flat lesions in immunocompromised individuals. HPV types 6, 11, 34, 39, 41–44 and 51–55 cause nonmalignant condylomata of the genital or respiratory mucosa. HPV types 16 and 18 cause epithelial dysplasia of the genital mucosa and are associated with the majority of in situ and invasive carcinomas of the cervix, vagina, vulva and anal canal. HPV6 and HPV11 are the causative agents for more than 90% of all condyloma (genital warts) and laryngeal papillomas.

Immunological studies in animals have shown that the production of neutralizing antibodies to papillomavirus antigens prevents infection with the homologous virus. The development of effective papillomavirus vaccines has been slowed by difficulties associated with the cultivation of papillomaviruses in vitro. The development of an effective HPV vaccine has been particularly slowed by the absence of a suitable animal model. Neutralization of papillomavirus by antibodies appears to be type-specific and dependent upon conformational epitopes on the surface of the virus.

Papillomaviruses are small (50–60 nm), nonenveloped, icosahedral DNA viruses that encode for up to eight early and two late genes. The open reading frames (ORFs) of the virus genomes are designated E1 to E7 and L1 and L2, where "E" denotes early and "L" denotes late. L1 and L2 code for virus capsid proteins. The early (E) genes are associated with functions such as viral replication and cellular transformation.

The L1 protein is the major capsid protein and has a molecular weight of 55–60 kDa. L2 protein is a minor capsid protein which has a predicted molecular weight of 55–60 kDa and an apparent molecular weight of 75–100 kDa as determined by polyacrylamide gel electrophoresis. Immunologic data suggest that most of the L2 protein is internal to the L1 protein. The L2 proteins are highly conserved among different papillomaviruses, especially the 10 basic amino acids at the C-terminus. The L1 ORF is highly conserved among different papillomaviruses.

The L1 and L2 genes have been used to generate vaccines for the prevention and treatment of papiromaviruses infections in animals. Zhou et al., (1991; 1992) cloned HPV type 16 L1 and L2 genes into a vaccinia virus vector and infected CV-1 mammalian cells with the recombinant vector to produce virus-like particles (VLP).

Recombinant baculoviruses expressing HPV6 L1, HPV11 L1, HPV16 L1, HPV18 L1, HPV31 L1 or HPV16 L2 ORFs have been used to infect insect Sf9 cells and produce L1 and L2 proteins. Western blot analyses showed that the baculovirus-derived L1 and L2 proteins reacted with antibody to HPV16. The baculovirus derived L1 forms VLPs.

Carter et al., (1991) demonstrated the production of HPV 16 L1 and HPV16 L2 proteins by recombinant strains of *Saccharomvces cerevisiae*. Carter et al. also demonstrated the production of HPV6b L1 and L2 proteins. The HPV6b L1 protein was not full-length L1 protein. The recombinant proteins were produced as intracellular as well as secreted products. The recombinant L1 and L2 proteins were of molecular weights similar to the native proteins. When the proteins were expressed intracellularly, the majority of the protein was found to be insoluble when the cells were lysed in the absence of denaturing reagents. Although this insolubility may facilitate purification of the protein, it may hamper analysis of the native epitopes of the protein.

Recombinant proteins secreted from yeast were shown to contain yeast-derived carbohydrates. The presence of these N-linked oligosaccharides may mask native epitopes. In addition, the secreted recombinant proteins may contain other modifications, such as retention of the secretory leader sequence.

The present invention is directed to the production of recombinant papillomavirus proteins having the immunity-conferring properties of the native papillomavirus proteins as well as methods for their production and use. The present invention is a series of synthetic virus-like particles useful in the characterization of human papillomavirus infection and assays employing the synthetic virus-like particles.

The invention involves the delineation of residues specific to HPV11 L1 which are required for binding neutralizing antibodies, and a modified HPV16 L1 gene with HPV11-like substitutions such that VLPs produced from the modified HPV16 L1 gene also bind HPV11 neutralizing monoclonal antibodies.

We previously demonstrated that HPV11 L1 residues $Gly^{131}$-$Tyr^{132}$ were responsible for the HPV11 specificity of binding of several HPV11 neutralizing monoclonal antibodies. Because the binding of these antibodies is conformationally dependent, it remained unanswered as to whether the epitope is continuous and comprised of residues located next to each other with conformation requiring VLP assembly, or discontinuous and comprised of residues well separated on the L1 linear sequence but which come into close proximity upon proper folding and assembly of particles. We scanned residues over a 20 residue stretch centered at $Gly^{131}$-$Tyr^{132}$, and identified five residues where substitution resulted in significant loss of binding of the neutralizing monoclonal antibodies, without affect on other HPV11 specific, VLP-dependent antibodies. This demonstrates that the epitope is continuous. This was confirmed by demonstrating that HPV11 substitutions at these positions into the HPV16 L1 sequence forms the basis of transfer of binding of these monoclonal antibodies to modified HPV16 VLPs.

The panel of neutralizing monoclonal antibodies for HPV11 was obtained from Neil Christensen (Pennsylvania State University, Hershey, Pa). The monoclonal antibodies in the panel are HPV11 specific and VLP-dependent. The antibodies may be distinguished from each other in terms of which amino acid residues affect binding of the individual antibodies, although there are overlapping positions for all the monoclonal antibodies. Additional antibodies used in these studies were also obtained from Dr. Neil Christensen.

These residues collectively define the epitope for antibodies known to neutralize HPV11 . We also demonstrate that substitution of these residues into equivalent positions of the HPV16 L1 sequence form the basis of transferring binding of these antibodies to modified HPV16 VLPs. The modified HPV16 VLPs may be used to develop HPV11 specific serological assays. Because of the high identity between HPV6 and HPV11 L1 sequences, present serological assays cannot distinguish responses between these two types very well. Modified HPV16 VLPs with a single HPV11 specific epitope and no cross-reactivity to HPV6 VLPs should be able to identify HPV11 immune responses upon infectivity or immunization.

This problem has not been solved in the past and, to our knowledge, is the first demonstration that a conformationlly dependent epitope is continuous.

There were two difficulties to overcome. First, the epitope is conformational, and conventional means of epitope mapping, binding to peptide fragments, could not be utilized. It was necessary to express any test L1 protein in a way that facilitated formation of virus-like particles which minic the virus structure. Second, the large number of L1 clones required for the mapping necessitated the generation of a facile means to express the test viral coat proteins.

Without isolation of a type-specific epitope, it would be difficult to distinguish HPV6 and HPV11 immune responses.

One use of the derivatized HPV16 VLP is as a reagent in a serological assay. Because most epitopes are shared between HPV6 and HPV11 VLPs, polyclonal sera to one competes with the binding of a type-specific monoclonal antibody to the other due to steric hindrance from the binding of antibodies to neighboring sites. There are very few cross-reactive epitopes between HPV16 and either HPV11 or HPV6. Therefore, presentation of an HPV11 specific epitope on an HPV16 VLP should eliminate the problem of steric competition from neighboring epitopes. Only the presence of antibody in a polyclonal response to the specifically transferred epitope should compete with monoclonal antibody binding.

SUMMARY OF THE INVENTION

This invention includes a series of synthetic virus-like particles (VLP) useful in the characterization of human papillomavirus types 11 and 16 infection and assays employing the synthetic particles.

BRIEF DESCRIPTION OF THE DRAWINGS

FIG. 2 shows the amino acid sequences or the L1 protein of HPV16 and several substituted clones (HPV16:5, HPV16:8 and HPV16:10). HPV16:5 contains five HPV11-like substitutions in positions demonstrated as critical to the binding of one or more HPV11 neutralizing MAbs. HPV16:8 contains three additional substitutions in residues non-critical for MAb binding. These latter substitutions are all alanine to glycine or alanine to proline substitutions, residues known to strongly perturb local structure. HPV16:10 contains a further two 11-like substitutions to generate a stretch of residues which completely matches the HPV11 L1 sequence over the region. FIGS. 3 and 4 show the results of MAb binding to VLPs produced from these clones.--.

DETAILED DESCRIPTION OF THE INVENTION

The present invention is a series of synthetic virus-like particles (VLP) useful in the characterization of human papillomavirus 11 infection and assays employing the synthetic virus-like particles, which may be used to monitor serological responses to HPV11 infection and immunization.

Papillomavirus infections occur in a variety of animals, including humans, sheep, dogs, cats, rabbits, monkeys, snakes and cows. Papillomaviruses infect epithelial cells, generally inducing benign epithelial or fibroepithelial tumors at the site of infection.

Papillomaviruses may be classified into distinct groups based on the host that they infect. Human papillomaviruses (HPV) are further classified into more than 60 types based on DNA sequence homology (for a review, see Papillomaviruses and Human Cancer, H. Pfister (ed.), CRC Press, Inc., 1990). Papillomavirus types appear to be type-specific immunogens in that a neutralizing immunity to infection to one type of papillomavirus does not confer immunity against another type of papillomavirus.

In humans, different HPV types cause distinct diseases. HPV types 1, 2, 3, 4, 7, 10 and 26–29 cause benign warts in both normal and immunocompromised individuals. HPV types 5, 8, 9, 12, 14, 15, 17, 19–25, 36 and 46–50 cause flat lesions in immunocompromised individuals. HPV types 6, 11, 34, 39, 41–44 and 51–55 cause nonmalignant condylomata of the genital and respiratory mucosa. HPV types 16 and 18 cause epithelial dysplasia of the genital tract and are associated with the majority of in situ and invasive carcinomas of the cervix, vagina, vulva and anal canal. HPV6 and HPV11 cause the majority of genital warts and laryngeal papillomas.

Immunological studies in animals have shown that the production of neutralizing antibodies to papillomavirus capsid proteins prevents infection with the homologous virus. The development of effective papillomavirus vaccines has been slowed by difficulties associated with the cultivation of papillomaviruses in vitro. The development of an effective HPV vaccine has been particularly slowed by the absence of a suitable animal model. Neutralization of papillomavirus by antibodies appears to be type-specific and dependent upon conformational epitopes on the surface of the virus.

Papillomaviruses are small (50–60 nm), nonenveloped, icosahedral DNA viruses that encode for up to eight early and two late genes. The open reading frames (ORFs) of the virus genomes are designated E1 to E7 and L1 and L2, where "E" denotes early and "L" denotes late. L1 and L2 code for virus capsid proteins. The early (E) genes are associated with functions such as viral replication and transformation.

The L1 protein is the major capsid protein and has a molecular weight of 55–60 kDa. L2 protein is a minor capsid protein which has a predicted molecular weight of 55–60 kDa and an apparent molecular weight of 75–100 kDa as determined by polyacrylamide gel electrophoresis.

The production of HPV16 L1, HPV16 L2, and HPV type 6 L1 proteins by recombinant strains of *Saccharomyces cerevisiae* has been reported. It would be useful to develop methods of producing large quantities of papillomavirus proteins of any species and type by cultivation of recombinant yeasts. It would also be useful to produce large quantities of papillomavirus proteins having the immunity-conferring properties of the native proteins, such as the conformation of the native protein. To achieve this latter goal it would be necessary to analyze the effect of numerous mutations in the L1 gene on the binding of antibodies of known properties (VLP dependent, cross-reactive, etc.)

The empirical scanning of natural or engineered peptide sequences for functional residues is inherently dependent upon expression of large numbers of sequence variants to assay their relative functional potency. The level of protein expression obtained can be particularly critical in the case of self-assembling viral structural proteins, because the efficiency of self-assembly frequently is concentration dependent. The insect baculovirus expression vector system has been widely used to study viral self-assembly, but it generally requires prior isolation and expansion of a plaque-purified recombinant viral stock to generate useful quantities of self-assembled particles. In examining a number of possibilities for expression of analytical levels of the L1 coat protein of Cottontail Rabbit and Human Type 11 Papillomaviruses, we found that even brief transient cotransfection of insect cells with baculovirus transfer vectors and viral DNA yielded assembled particles which were immunologically indistinguishable from particles previously obtained from plaque purified stocks (Benincasa et. al. 1996. Rapid, high-level transient expression of papillomavirus-like particles in insect cells. BioTechniques 20,890–895). Within six days of plasmid/viral DNA cotransfection of Sf9 cells, at least 1–2 μg of assembled L1 particles/100 mm plate could be demonstrated. This level of expression is more than sufficient to assay functionality, and has several advantages over comparable mammalian cell transient expression systems.

To define neutralizing epitopes in HPV infections, we need to identify the amino acid residues that confer antigenic type-specificity on human papillomavirus subtypes (Christensen, N. D., et. al. 1990, Monoclonal antibody-mediated neutralization of infectious human papillomavirus type 11). Many of the type-specific epitopes are conformationally-dependent and are detectable only upon VLP assembly. The L1 structural coat protein of several animal and human papillomaviruses has been demonstrated to efficiently self-assemble when expressed in insect cells via recombinant baculovirus strains (Christensen, N. D., et al., 1994, Assembled baculovirus-expressed human papillomavirus type 11 L1 capsid protein virus-like particles are recognized by neutralizing monoclonal antibodies and induce high titres of neutralizing antibodies. J. Gen. Virol. 75, 2271–2276). The time and labor involved in the generation of recombinant phage precludes the use of this method to screen a large number of VLP variants produced through site-directed mutagenesis. However, we previously observed that when expressed in the baculovirus system, a recombinant protein is detectable as a secreted product in μg/ml quantities within 5–7 days of the initial transfection of insect cells with plasmid and viral DNAs. Based upon this observation, we examined whether sufficient quantities of papillomavirus L1 protein would accumulate to allow self-assembly into VLPs upon transient expression, particularly if a more efficient baculovirus transfection system such as the Baculogold™ (Pharmingen, San Diego, Calif.) system were utilized. Employing a rapid 6-day transient transfection protocol, the L1 coat protein of numerous papillomavirus types, properly assembled into VLPs, was produced. Extracts prepared from transiently transfected cells with CRPV or HPV11 L1 gene constructs contained immunogenic material recognized by type-specific and VLP dependent monoclonal antibodies generated against either CRPV or HPV11 VLPs. The transiently expressed material was not cross-reactive with other type-specific antibodies, and recognition was sensitive to alkaline denaturation, further demonstrating fidelity in VLP formation.

We previously identified HPV11 L1 residues $Gly^{131}$-$Tyr^{132}$ as responsible for the type-specific binding of several HPV11 neutralizing monoclonal antibodies (Ludmerer et. al. 1996. Two amino acid residues confer type specificity to a neutralizing, conformationally dependent epitope on human papillomavirus type 11. *J. Virol.* 70, 4791–4794). To map the HPV11 neutralizing epitope, we individually mutated HPV11 at the residues where the sequence diverges from the HPV16 sequence over a 20 residue stretch centered at $Gly^{131}$-$Tyr^{132}$. The positions were mutated to match the HPV16 sequence. Using the Sf9 transient expression system described above, these mutant HPV11 L1 genes were expressed and analyzed for binding by HPV11specific monoclonal antibodies.

The following examples are provided to further define the invention without, however, limiting the invention to the particulars of these examples.

EXAMPLE 1
Generation of test expression constructs.

The HPV11 L1 structural gene was cloned from clinical isolates using PCR with primers designed from the published L1 sequence. The L1 gene was subsequently subcloned both into BlueScript (Pharmacia) for mutagenesis, and pVL1393 (Stratagene) for expression in Sf9 cells.

Mutations were introduced into the L1 gene using Amersham Sculptor in vitro mutagenesis kit. The appearance of the desired mutation was confirmed by sequencing, and the mutated gene subdoned into pVL1393 for expression in Sf9 cells.

The HPV16 L1 structural gene was subdoned both into BluScript (Pharmacia) for mutagenesis, and pVL1393 (Stratagene) for expression in Sf9 cells. Mutations were generated using the Amersham Sculptor in vitro mutagenesis kit, verified by sequencing, and subcloned into pVL1393 for expression in Sf9 cells.

EXAMPLE 2
Transient Expression of L1 VLPs in SF9 cells.

SF9 cells were transfected using BaculoGold Transfection kit (Pharmingen). Transfections were done essentially according to the manufacturer's instructions with the following modifications. $8 \cdot 10^8$ Sf9 cells were transfected in a 100 mM dish, with 4 $\mu$g of BaculoGold DNA and 6 ug of test DNA. Cells were harvested after 6 days and assayed for VLP production.

EXAMPLE 3
Preparation of SF9 extracts and ELISA assays.

Cells were harvested six days after transfection, by scraping followed by low speed centrifugation. Cells were resuspended in 300 ml of breaking buffer (1 M NaCl, 0.2 M Tris pH 7.6) and homogenized for 30" on ice using a Polytron PT 1200 B with a PT-DA 1205/2-A probe (Brinkman) in a Falcon 1259 tube. Samples were spun at 2500 rpm for 3 minutes to pellet debris. Tubes were washed with an additional 150 ml of breaking buffer, supernatants collected in a 1.5 ml microfuge tube, and respun for 5 minutes in an Eppendorf microfuge (Brinkman). Supernatants were collected and stored at 4° C. until use. ELISA assays typically were performed the same day.

5 ml of extract was diluted into 50 ml of 1% BSA in PBS (phosphate buffered saline; 20 mM NaPO$_4$, pH 7.0, 150 mM NaCl) and plated onto a polystyrene plate. The plate was incubated overnight at 4° C. Extracts were removed and the plate blocked with 5% powdered milk in PBS. All subsequent wash steps were performed with 1% BSA in PBS. The plate was incubated at room temperature with primary antibody for 1 hour. Primary antibodies, monoclonal antibodies generated against HPV11 VLPs, were obtained as ascites stock from Dr. Neil Christensen (Pennsylvania State University). They were diluted $10^5$ in 1% BSA PBS before use. After washing, plates were incubated for 1 hour with secondary antibody. The secondary antibody, peroxidase labeled Goat anti-Mouse IgG (g), was purchased from Kirkegaard & Perry Laboratories, Inc. and used at $10^3$ dilution in 1% BSA in PBS. After a final washing, an alkaline phosphatase assay was performed and absorbance read at 405 nm.

EXAMPLE 4
HPV11 scan

To map the residues critical for an HPV11 specific neutralizing epitope, we take advantage of two conditions. First of all, we used a panel of monoclonal antibodies which are specific for HPV11 L1 and recognize L1 only when assembled into a VLP. Among these five antibodies, 4 have been demonstrated to neutralize HPV11 in the Kreider Xenograft system (Kreider et al., 1987, J. Virol. 61:590–593)

We previously demonstrated that the type-specificity to binding of three of the neutralizing MAbs is due to Gly$^{131}$-Tyr$^{132}$ of the HPV11 L1 sequence, and that the fourth neutralizing monoclonal antibody binds a different site. Because the epitope is conformational, a more complete description of the epitope is desired. In particular, it was not known if the epitope is continuous, with contact residues in close proximity in the linear sequence and conformation requiring proper L1 folding and assembly, or discontinuous, with the contact residues at diverse positions of the linear sequence with positional proximity emerging only after assembly.

We reasoned that if the epitope is continuous, then several residues critical for binding should be located within a short distance of the Gly$^{131}$-Tyr$^{132}$ pair. Because a typical linear epitope spans 10–12 residues, we scanned residues within 12 positions of Gly$^{131}$-Tyr$^{132}$ for an approximately 25-residue stretch. Because binding is specific for HPV11 VLPs, we focused on those residues where the sequence diverges between HPV11 and HPV16. Beyond this 25 residue region the homology between the two sequences increase dramatically. Substitutions into HPV11L1 were selected from the HPV16 sequence to minimize the possibility that the substitution would result in a more general perturbation on VLP structure.

To determine the affect on binding of any particular residue, both HPV11 and the corresponding HPV11 derivative were expressed in the transient expression system. An ELISA was performed using the panel of HPV11 specific monoclonal antibodies, and results between the two compared. L1 production was normalized with monoclonal antibody H6.C6. H6.C6 antibody is cross-reactive with HPV11, and its epitope is linear and recognized independently of VLP formation. Thus it measures L1 production.

Results are put through a double normalization. First, the ratio of absorbance of the test antibody to H6.C6 is calculated for the test position. The same ratio is determined for HPV11 and divided into the ratio for the test position. Thus a double ratio near 1 means that there is no detectable difference in antibody binding to the test clone relative to HPV11. A double ratio less than one means that the test antibody binds more poorly to the test clone than wild-type. In theory, a ratio greater than 1 means that the antibody binds better to the test clone than to HPV11. In practice this was not observed. A ratio in the range of 0.1 to 0.2 is essentially background, meaning we cannot detect binding of the antibody to the mutant VLP.

The positions in HPV11 L1 between residue 120 and 145 which differ from HPV16 L1 were individually substituted with the HPV16 residue. Clones were expressed in SF9 cells through a Baculovirus expressing recombinant, and affect of binding by the panel of HPV11 specific monoclonal antibodies determined (Table 1). Only substitutions which resulted in binding impairment for one or more antibodies are included in the table. Note that the binding of H11.A3.2 and H11.H3 is not impaired upon any substitution. Both are HPV11 specific, VLP dependent MAbs demonstrated to bind different regions of VLPs than H11.B2, H11.F1, and H11.G5. Binding by H11.A3.2 and H11.H3 verifies the assembly of VLPs, and demonstrates that the effect of substitution is specific for antibodies binding at this region.

TABLE 1

| Position | H11.A3.2 | H11.B2 | H11.F1 | H11.G5 | H11.H3 |
|---|---|---|---|---|---|
| Y123L | 0.65 | 0.48 | 0.17 | 0.22 | 1.34 |
| G130S | 0.88 | 0.44 | 0.08 | 0.11 | 1.3 |
| G131A | 0.99 | 0.11 | 0.08 | 0.10 | 1.03 |
| Q138V | 0.93 | 0.45 | 0.62 | 1.05 | 0.83 |
| V142E | 0.93 | nd | 0.40 | 0.57 | 1.27 |

EXAMPLE 5
Transfer of the HPV11 Neutralizing Epitope to HPV16

Figure 1:
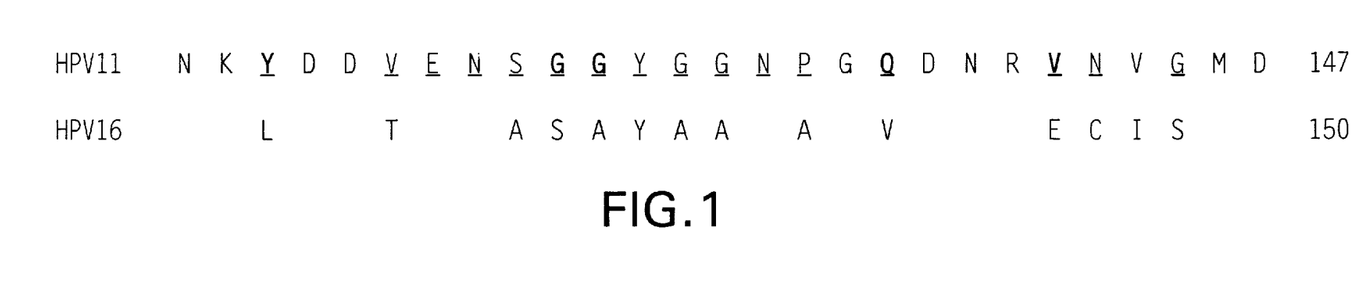
FIG. 1 shows the amino acid sequences of the HPV11 and HPV16 L1 protein in the region mutagenized (residues 121 through 147), and also shows the specific substitutions made in this study. These sequences are available in the EMBL Gene Bank. The lower line shows the differences with the HPV L1 sequence over the homologous stretch. Note that the alignment shifts the HPV16 sequence three residues with respect to HPV11. A $G^{131}$:$Y^{132}$ double substitution into the HPV6 L1 sequence was previously demonstrated to be necessary and sufficient to transfer binding of HPV11 neutralizing MAbs to HPV6 VLPs. Substitutions into the HPV11 sequence were individually made and analyzed for MAb binding at all underlined positions. Where the two sequences differ, HPV16-like substitutions were made. Otherwise alanine was substituted. Substitutions which resulted in loss of binding of one or more HPV11 neutralizing MAb are indicated by bold-face.
Figure 2:
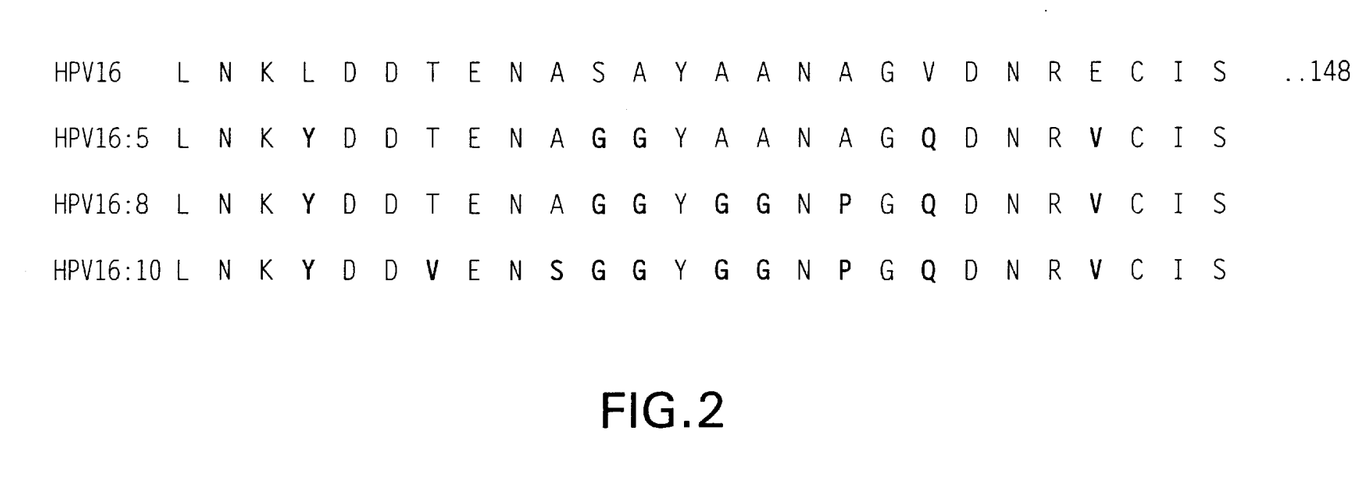
Figure 3:
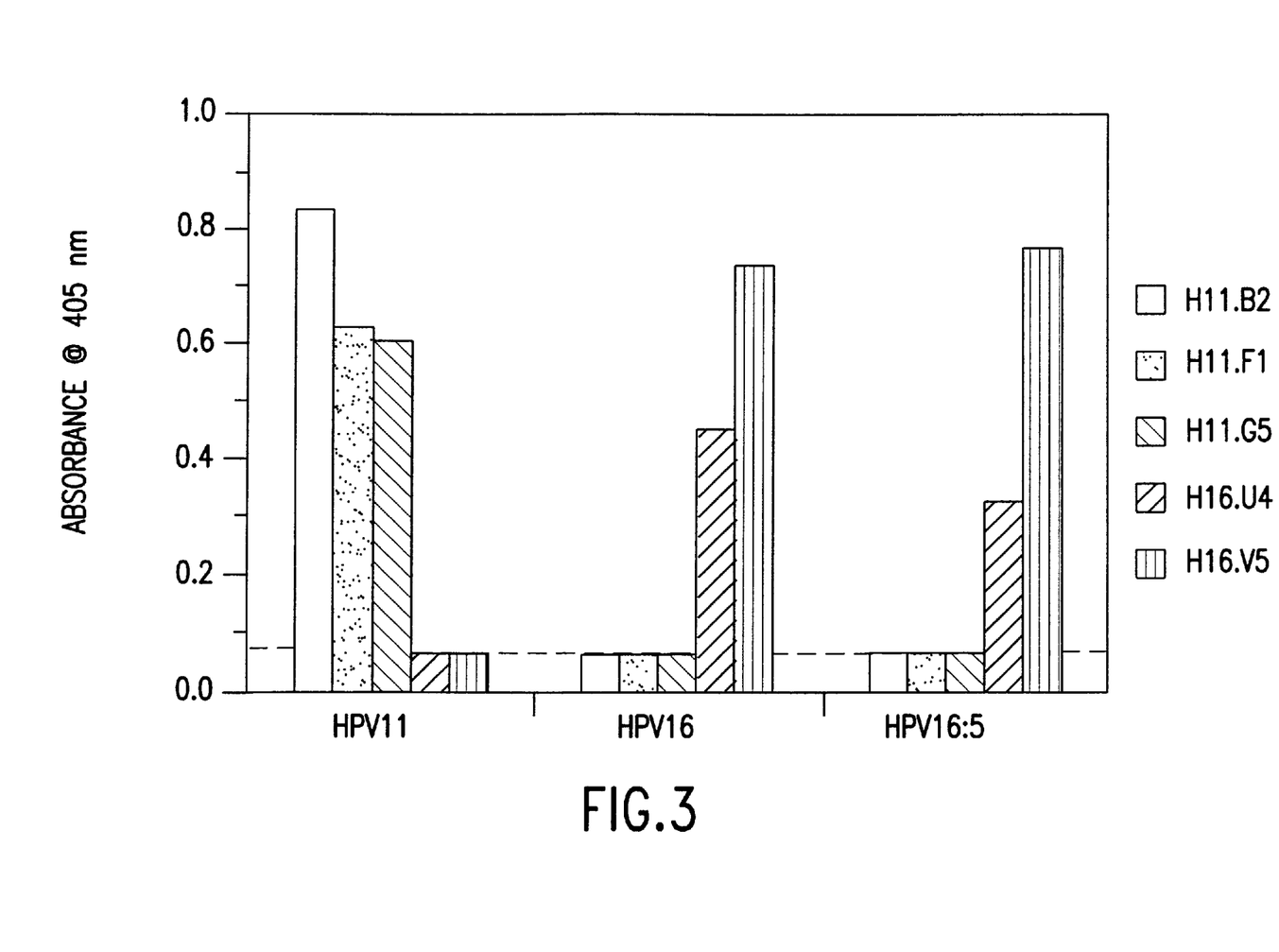
FIG. 3 shows that amino acid substitutions at critical positions are not sufficient to transfer HPV11 monoclonal antibody (MAb) binding to HPV16 VLPs. VLPs for HPV11, HPV16 and HPV16:5 (HPV16 with five 11-like substitutions) were expressed in Sf9 cells and assayed for binding by HPV11 or HPV16 specific MAbs. The five substitutions into HPV16 L1 are without affect on the binding of two HPV16 specific MAbs, but also of not result in transfer of HPV11 MAb binding. MAbs were used as $10^{-5}$ dilution of ascites stock. Binding to HPV11 extract by MAb CRPV.5A, a CRPV-specific antibody which does not cross-react with human papillomavirus types, is shown as a dashed line.
Figure 4:
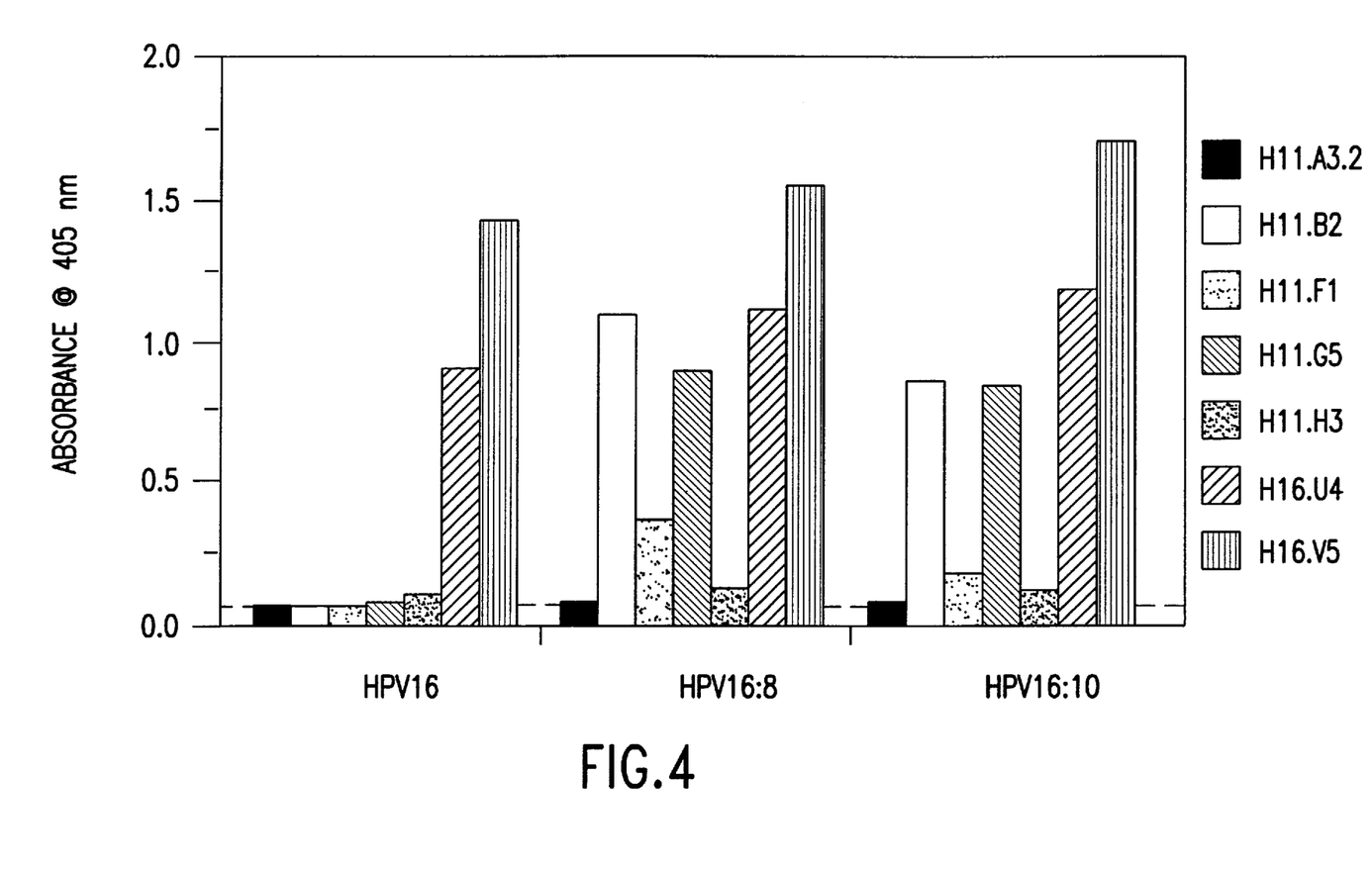
FIG. 4 shows that eight amino acid substitutions into the HPV16 L1 sequence confers HPV11 monoclonal antibody binding and demonstrate a continuous, conformational epitope. VLPs for HPV16, HPV16:8, and HPV16:10 were expressed in Sf9 cells and assayed for binding by HPV11 or HPV16 specific MAbs. HPV16:8 contains five critical substitutions, and three additional A to G or A to P substitutions in positions individually shown not to be critical for binding (see FIG. 2). HPV16:8 VLPs, but not HPV16 VLPs, bind HPV11 specific MAbs H11.B2, H11.F1 and H11.G5. Note that binding of MAbs H11.A3 and H11.H3, both of which were shown not to be affected by substitutions within this stretch, is not observed. MAbs 11.B2, H11.F1, and H11.G5, whose binding is transferred to HPV16:8 VLPs, bind only assembled virus or VLPs. These three MAbs were previously demonstrated to neutralize infectious HPV11 virus in the mouse xenograph assay. HPV16:10 VLPs, which contain two additional HPV11 substitutions to make the entire stretch match the HPV11 sequence, do not show any additional level of HPV11 MAb binding. MAbs were used as $10^{31\ 5}$ dilution of ascites stock. Bonding to HPV11 extract by MAb CRPV.5A, a CRPV-specific antibody which does not cross-react with human papillomavirus types, is shown as a dashed line.

Based upon the studies in Example 4, we mutated the HPV16 L1 gene at amino acid residues 126, 133, 134,141, and 145 to match the HPV11 L1 sequence. We designate this clone as HPV16:5 To our surprise, we saw no binding of HPV11 monoclonal antibodies to VLPs produced from this clone. We reasoned that we had provided the important contact positions, but were not presenting this highly conformationally dependent epitope correctly. We noted that the HPV11 L1 sequence contains the residues $G^{133}$, $G^{134}$, and $P^{136}$, where the HPV16 L1 sequence has alanine in the three equivalent positions 136, 137, and 139. Glycine and proline residues can introduce structural perturbations. Although individual substitutions into the HPV11 L1 sequence at these positions were without effect, we reasoned that three such changes right at the region of the epitope may collectively affect epitope presentation. Using clone HPV16:5 as a template, we generated a clone that had the further substitutions A136G, A137G, and A139P to create clone HPV16:8. This clone produced VLPs which bind HPV11 antibodies H11.B2, H11.F1, and H11.G5. Binding of two separate HPV16 VLP dependent monoclonal antibodies is not affected. Using HPV16:8 as a template, we generated a third clone which has T129V and A132S substitutions to generate HPV16:10. This clone is identical to HPV11 L1 over the region evaluated, but these latter two positions were shown to be nonessential for binding. Consistent with this, clone HPV16:10 shows no further improvement in MAb binding relative to HPV16:8. Binding is normalized to L1 production using monoclonal antibody H16.D9, which binds an internal linear epitope that is presented only upon denaturation of the sample. The table is divided into two sets because the pairs of samples were transfected and assayed separately. Binding of HPV11 neutralizing monoclonal antibodies to modified HPV16 VLPs

| Clone | H11.A3.2 | H11.B2 | H11.F1 | H11.G5 | H11.H3 | H16.U4 | H16.V5 |
|---|---|---|---|---|---|---|---|
| HPV16 | 0.07 | 0.07 | 0.07 | 0.07 | 0.13 | 1.16 | 1.7 |
| HPV16:8 | 0.10 | 1.51 | 0.50 | 1.27 | 0.16 | 1.60 | 2.17 |
| HPV16:10 | 0.10 | 1.26 | 0.26 | 1.20 | 0.17 | 1.70 | 2.40 |
| HPV16 | 0.12 | 0.12 | 0.12 | 0.12 | 0.12 | 1.0 | 1.6 |
| HPV16:5 | 0.11 | 0.11 | 0.12 | 0.11 | 0.11 | 0.47 | 0.85 |

Clone HPV16:8 also demonstrates the mapping of the HPV11 neutralizing epitope, and the potential to use this information to transfer it to a distal surface. In principle, this mapping data could be the basis of transfer to an even more distal surface, such as CRPV VLPs. Such a reagent could be used in the same way as we described for HPV16:8 VLPs in a serological assay, with the added advantage that it could be used to screen the immunological response of individuals immunized with multiple VLP types which include HPV6, HPV11 and HPV16 VLPs.

EXAMPLE 6
Monitoring Serological Responses to HPV11 Infection or Immunization HPV16 modified VLPs are used to determine the presence of an immune response to HPV11 following viral infection or immunization with HPV11 VLPs. HPV16 modified VLPs which present the HPV11 neutralizing epitope will be coated onto the well of a microtitre plate in native form. Following blocking, an HPV11 monoclonal antibody which binds this epitope, H11.B2, H11.F1, or H11.G5, will be incubated in ELISA format with increasing amounts of HPV11 polyclonal sera, HPV6 polyclonal sera, and test polyclonal sera. Binding of the HPV11 monoclonal antibody will be visualized using a rabbit anti-mouse IgG secondary antibody. Alternatively, it can be labeled with $I^{125}$, or coupled directly to horse radish peroxidase or alkaline phosphatase, or another standard ELISA visualization protocol. Increasing amounts of polyclonal HPV11 sera will compete with binding until the signal eventually is reduced to background level. Polyclonal HPV6 sera will not compete, or the competition will be significantly reduced from that observed with HPV11 polyclonal sera. Competition with the test sera at levels comparable to HPV11 polyclonal sera will demonstrate an immune response to HPV11. Lack or significant reduction of competition will demonstrate lack of or a weak immune response to HPV11.

EXAMPLE 7
Transient expression of VLPs in Sf9 cells

The HPV11 L1 structural gene was cloned from clinical isolates using the Polymerase Chain Reaction (PCR) with primers designed from the published L1 sequence (8,17). The CRPV L1 structural gene was cloned by PCR from viral genomic DNA. The L1 genes were subcloned into pVL1393 (Stratagene) for expression in Sf9 cells.

Sf9 cells were cotransfected using the BaculoGold Transfection kit (Pharmingen, San Diego, Calif.). Transfections were done according to the manufacturer's instructions with the following modification: $8.10^6$ Sf9 cells were transfected in a 100 mm dish, with 4 µg of BaculoGold viral DNA and 6 µg of test plasmid DNA. Cells were harvested after 6 days, except where otherwise specified, and assayed for VLP production by Western Blot or ELISA assay (below).

EXAMPLE 8
Preparation of Sf9 extracts and ELISA assays.

Cells were harvested six days after transfection. Plates were scraped to resuspend cells, and the cells were collected by low speed centrifugation. Cells were resuspended in 300 µl of breaking buffer (1 M NaCl, 0.2 M Tris pH 7.6) and homogenized for 30 seconds on ice using a Polytron PT 1200 B with a PT-DA 1205/2-A probe (Brinkman) in a Falcon 2059 tube. Samples were spun at 2500 rpm in a GPR centrifuge (Beckman Instruments, Inc. Palo Alto, Calif.) for 3 minutes to pellet debris. Tubes were washed with an additional 150 ml of breaking buffer, supernatants collected in a 1.5 ml microfuge tube, and respun for 5 minutes in an Eppendorf microfuge (Brinkinan). ELISA assays were begun the same day.

5 ml of extract was diluted into 50 ml of 1% BSA in phosphate-buffered saline solution (PBS), aliquoted onto a 96 well Immulon 2 microtiter plate (Dynatech Laboratories, Inc.), and incubated overnight at 4° C. Extracts were removed and the plate blocked with 5% powdered milk/PBS. All subsequent wash steps were performed with 1% BSA/PBS. The plate was incubated at room temperature with primary antibody for 1 hour. The primary antibodies, monoclonal antibodies CRPV.5A and H11.F1, were obtained as ascites stock from Dr. Neil Christensen. They are VLP-dependent and type specific antibodies which recognize CRPV and HPV11 VLPs respectively (Neil Christiansen, personal communication). They were diluted $10^5$-fold in 1% BSA/PBS before use. After washing in 1% BSA/PBS, plates were incubated for 1 hour with secondary antibody, peroxidase labeled Goat anti-Mouse IgG (g) (Kirkegaard & Perry Laboratories, Inc.) and used at $10^3$ dilution in 1% BSA in PBS. After a final washing, an alkaline phosphatase assay was performed and absorbance read at 405 nm.

What is claimed:

1. Synthetic HPV16 virus-like particles selected from the group HPV16:8, HPV16:8L126Y, HPV16:8S133G, HPV16:8A134G, HPV16:8A136G, HPV16:8A137G, HPV16:8A139P, HPV16:8V141Q and HPV16:8E145V.

* * * * *

```
                         SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
         (A) LENGTH: 27 amino acids
         (B) TYPE: amino acid
         (C) STRANDEDNESS: single
         (D) TOPOLOGY: linear (ii) MOLECULE TYPE: peptide (v) FRAGMENT TYPE: internal (xi) SEQUENCE DESCRIPTION: SEQ ID NO:1:

Asn Lys Tyr Asp Asp Val Glu Asn Ser Gly Gly Tyr Gly Gly Asn Pro
 1               5                  10                  15

Gly Gln Asp Asn Arg Val Asn Val Gly Met Asp
             20                  25

(2) INFORMATION FOR SEQ ID NO:2:

(i) SEQUENCE CHARACTERISTICS:
         (A) LENGTH: 27 amino acids
         (B) TYPE: amino acid
         (C) STRANDEDNESS: single
         (D) TOPOLOGY: linear (ii) MOLECULE TYPE: peptide (v) FRAGMENT TYPE: internal (xi) SEQUENCE DESCRIPTION: SEQ ID NO:2:

Asn Lys Leu Asp Asp Thr Glu Asn Ala Ser Ala Tyr Ala Ala Asn Ala
 1               5                  10                  15

Gly Val Asp Asn Arg Glu Cys Ile Ser Met Asp
             20                  25

(2) INFORMATION FOR SEQ ID NO:3:

(i) SEQUENCE CHARACTERISTICS:
         (A) LENGTH: 26 amino acids
         (B) TYPE: amino acid
         (C) STRANDEDNESS: single
         (D) TOPOLOGY: linear (ii) MOLECULE TYPE: peptide (v) FRAGMENT TYPE: internal (xi) SEQUENCE DESCRIPTION: SEQ ID NO:3:
```

-continued

```
Leu Asn Lys Leu Asp Asp Thr Glu Asn Ala Ser Ala Tyr Ala Ala Asn
 1               5                  10                  15

Ala Gly Val Asp Asn Arg Glu Cys Ile Ser
            20                  25

(2) INFORMATION FOR SEQ ID NO:4:

(i) SEQUENCE CHARACTERISTICS:
                  (A) LENGTH: 26 amino acids
          (B) TYPE: amino acid
          (C) STRANDEDNESS: single
          (D) TOPOLOGY: linear
    (ii) MOLECULE TYPE: peptide
     (v) FRAGMENT TYPE: internal
    (xi) SEQUENCE DESCRIPTION: SEQ ID NO:4:
Leu Asn Lys Tyr Asp Asp Thr Glu Asn Ala Gly Gly Tyr Ala Ala Asn
 1               5                  10                  15

Ala Gly Gln Asp Asn Arg Val Cys Ile Ser
            20                  25

(2) INFORMATION FOR SEQ ID NO:5:

(i) SEQUENCE CHARACTERISTICS:
                  (A) LENGTH: 26 amino acids
          (B) TYPE: amino acid
          (C) STRANDEDNESS: single
          (D) TOPOLOGY: linear
    (ii) MOLECULE TYPE: peptide
     (v) FRAGMENT TYPE: internal
    (xi) SEQUENCE DESCRIPTION: SEQ ID NO:5:
Leu Asn Lys Tyr Asp Asp Thr Glu Asn Ala Gly Gly Tyr Gly Gly Asn
 1               5                  10                  15

Pro Gly Gln Asp Asn Arg Val Cys Ile Ser
            20                  25

(2) INFORMATION FOR SEQ ID NO:6:

(i) SEQUENCE CHARACTERISTICS:
                  (A) LENGTH: 26 amino acids
          (B) TYPE: amino acid
          (C) STRANDEDNESS: single
          (D) TOPOLOGY: linear
    (ii) MOLECULE TYPE: peptide
     (v) FRAGMENT TYPE: internal
    (xi) SEQUENCE DESCRIPTION: SEQ ID NO:6:
Leu Asn Lys Tyr Asp Asp Val Glu Asn Ser Gly Gly Tyr Gly Gly Asn
 1               5                  10                  15

Pro Gly Gln Asp Asn Arg Val Cys Ile Ser
            20                  25
```